United States Patent [19]

Hupe et al.

[11] Patent Number: 5,316,954
[45] Date of Patent: May 31, 1994

[54] METHODS AND APPARATUS FOR PROCESSING LIQUIDS

[75] Inventors: Klaus-Peter Hupe, Baden-Baden; Fred Strohmeier, Rheinmuenster; Hans-Peter Zimmermann, Karlsbad; Werner Eberhardt, Ueberherrn, all of Fed. Rep. of Germany

[73] Assignee: Hewlett-Packard Company, Palo Alto, Calif.

[21] Appl. No.: 972,077

[22] Filed: Nov. 5, 1992

Related U.S. Application Data

[63] Continuation of Ser. No. 687,178, Apr. 18, 1991, abandoned.

[30] Foreign Application Priority Data

Jul. 9, 1990 [EP] European Pat. Off. ........ 90113068.2

[51] Int. Cl.$^5$ .......................................... G01N 33/00
[52] U.S. Cl. .......................... 436/89; 436/43; 436/45; 422/64; 422/81; 422/116; 422/68.1
[58] Field of Search ................ 422/64, 70, 81, 116, 422/68.1; 436/43, 45, 52, 89

[56] References Cited

U.S. PATENT DOCUMENTS

| | | | |
|---|---|---|---|
| 4,037,248 | 5/1978 | Miles | 358/13 |
| 4,311,667 | 1/1982 | Gocho | 422/64 |
| 4,340,390 | 7/1982 | Collins et al. | 422/64 |
| 4,478,095 | 10/1984 | Bradley et al. | 422/64 X |
| 4,656,006 | 4/1987 | Assmann et al. | 422/64 X |
| 4,836,038 | 6/1989 | Baldwyn | 422/64 X |
| 5,039,488 | 8/1991 | Kohr | 436/89 X |
| 5,156,809 | 10/1992 | Hupe et al. | 436/45 X |
| 5,164,318 | 11/1992 | Sato et al. | 422/64 X |
| 5,213,761 | 5/1993 | Sakagami | 422/64 X |

FOREIGN PATENT DOCUMENTS

| | | |
|---|---|---|
| 0122722 | 10/1984 | European Pat. Off. . |
| 0143097 | 5/1985 | European Pat. Off. . |
| 0279882 | 8/1988 | European Pat. Off. . |
| 2194176A | 2/1988 | United Kingdom . |

OTHER PUBLICATIONS

Wada, et al., *Review of Scientific Instruments*, 1983, vol. 54, No. 11, pp. 1569–1572.
Kretz, et al., *Hewlett-Packard Journal*, 1984, 21–24.

*Primary Examiner*—James C. Housel
*Assistant Examiner*—Maureen M. Wallenhorst
*Attorney, Agent, or Firm*—Woodcock Washburn Kurtz Mackiewicz & Norris

[57] ABSTRACT

Apparatus and methods for processing liquids are provided. The apparatus include open-ended, hollow reactor compartments which are detachably connected to receptor ends of tube systems. In preferred embodiments, a portion of the tube system is fixed to a rotor arm which can be rotated in a circle and moved up and down. Another portion of the tube system is coupled to a metering syringe which serves for drawing in or ejecting fluids into or from the reactor compartment and/or the tube system. A plurality of process stations such as bottles containing reagents or solvents can be arranged on a circular tray such that they can be accessed by the reactor compartment or by the receptor end if the reactor compartment has been detached from the tube system. The invention can be used, for example, for automatic protein sequencing, whereby the proteins to be sequenced are held in place by a matrix in the reactor compartment.

19 Claims, 3 Drawing Sheets

METHODS AND APPARATUS FOR PROCESSING LIQUIDS

This is a continuation of application Ser. No. 687,178, filed Apr. 18, 1991 now abandoned.

FIELD OF THE INVENTION

The present invention relates to methods and apparatus for processing liquids and, more particularly, to apparatus which are useful in processes which require the handling and processing of a plurality of liquids, reagents, and solvents in a plurality of recurring steps.

BACKGROUND OF THE INVENTION

A commonly used process for the determination of amino acid sequences in proteins is disclosed by P. Edman and G. Begg, European Journal of Biochemistry, Vol. 1, 1967, pages 80-91. In this process, which is based upon the degradation of phenylisothiocyanate, the free N-terminal alpha-amino group of a protein is first converted into a phenylthiocarbamyl (PTC) derivative through coupling with phenylisothiocyanate (PITC) in a basic environment. The phenylthiocarbamyl derivative is cleaved in a strongly acidic environment and is cyclized through formation of a thiazolinone derivative (ATZ), which then can be converted by treatment with aqueous acid into the more stable phenylthiohydantoin (PTH) derivative. The alpha-amino group of the next in the chain of amino acids is thus set free and can be subjected to a further degradation. The PTH amino acid can be identified by using liquid chromatography.

EP-A-279882 discloses one apparatus which can be used for automatically sequencing proteins according to the above-described degradation scheme. The disclosed apparatus comprises a cup-shaped reactor vessel which spins around its longitudinal axis, and a movable pipette which connects with a syringe such that liquid can be sucked into or expelled from the pipette. The movable pipette is used to deposit various reagents and solvents on the wall of the spinning reactor vessel, where they come into contact with a sample of, for example, proteins or peptides to be sequenced. The movable pipette is also used for removing reaction products and excess products from the reactor vessel. Due to the high rotation speed of the reactor vessel (typically several hundred revolutions per minute), special designs regarding drive and bearing of the reactor vessel are required.

It is accordingly one object of the present invention to provide an apparatus for processing liquid which has a simpler design and which avoids the problems associated with a spinning reactor vessel.

SUMMARY OF THE INVENTION

The present invention provides methods and apparatus for processing liquids. The apparatus comprises a tube system having a first end, a hollow, open-ended reactor compartment having one of its ends coupled to or decoupled from the first end of the tube system, and a metering device which can be coupled to a second end of the tube system such that selectable amounts of fluids can be taken into or ejected from the tube system and/or the reactor compartment by careful control of the metering device.

Preferred apparatus further comprise a plurality of process stations positioned proximate the first end of the tube system, as well as positioning means for selectably positioning the first end of the tube system at any of the process stations. At such process stations, fluids required for sample processing can be taken in and reaction products and/or waste products can be removed.

In preferred embodiments, the reactor compartment is detachable from the end of the tube system so that fluids can be taken in or ejected from the tube system without passing through the reactor. When the reactor has again been attached to the tube system, the liquid can be introduced into the reactor by appropriate control of the metering device.

Preferably, the positioning means comprises a movable robotic arm which can be rotated in a circle on which the various process stations are arranged. The robotic arm can also be raised or lowered so that the reactor compartment or the end of the tube system to which it is connectable can dip into liquid-containing bottles or so that the reactor compartment can be stored in an oven. The reactor compartment is preferably filled with a matrix which can hold in place any substances to be processed. As an alternative to a rotatable positioning means, one could also use an X,Y-drive which operates using a two-dimensional coordinate system.

The invention thus provides a mechanically simple and rugged device for processing liquid which avoids the drawbacks of a spinning reactor vessel. The reactor compartment may, for example, be simply a pipette tip which can be attached to a normal pipette. The reactor is thus inexpensive and disposable. The apparatus according to the invention has the further advantage that it is small, reliable, and easy to use. Furthermore, it permits delivery of very small liquid volumes via very short flow paths. It has a low consumption of reagents and solvents and is inexpensive to manufacture. Also, the apparatus of the invention allows accommodation and operation of more than one reactor compartment.

The apparatus of the invention can be used not only for protein sequencing, but also for peptide or oligonucleotide synthesis, or for liquid-liquid extraction, liquid-solid extraction, hydrolysis of proteins, or other procedures as they are applied to prepare and manipulate samples prior to the various analytical methods for analyzing substances.

In the case of protein sequencing, the apparatus of the invention can easily be coupled to a liquid chromatograph wherein the PTH amino acids are analyzed. The coupling to the liquid chromatograph is preferably accomplished by means of a double-needle comprising two hollow needles of different lengths which are rigidly connected to each other. One of the needles is connected to the tube system of the liquid processing apparatus, while the other needle can be coupled to the liquid chromatograph. Since the openings of the two needles are at different levels, liquid can be delivered from the processing apparatus into a vial through the first needle and then transferred from this vial through the second needle into an injection loop of the liquid chromatograph without requiring switching-over processes.

As a further advantage of the invention, the apparatus permits easy flushing of the system with a gas in order to clean and/or dry those portions which have come in contact with the various liquids. The gas can be supplied through the metering device to the connected tube system and the reactor compartment attached thereto.

BRIEF DESCRIPTION OF THE DRAWINGS

The numerous objects and advantages of the present invention may be better understood by those skilled in the art by reference to the accompanying figures, in which.

DETAILED DESCRIPTION OF THE DRAWINGS

Figure 1:
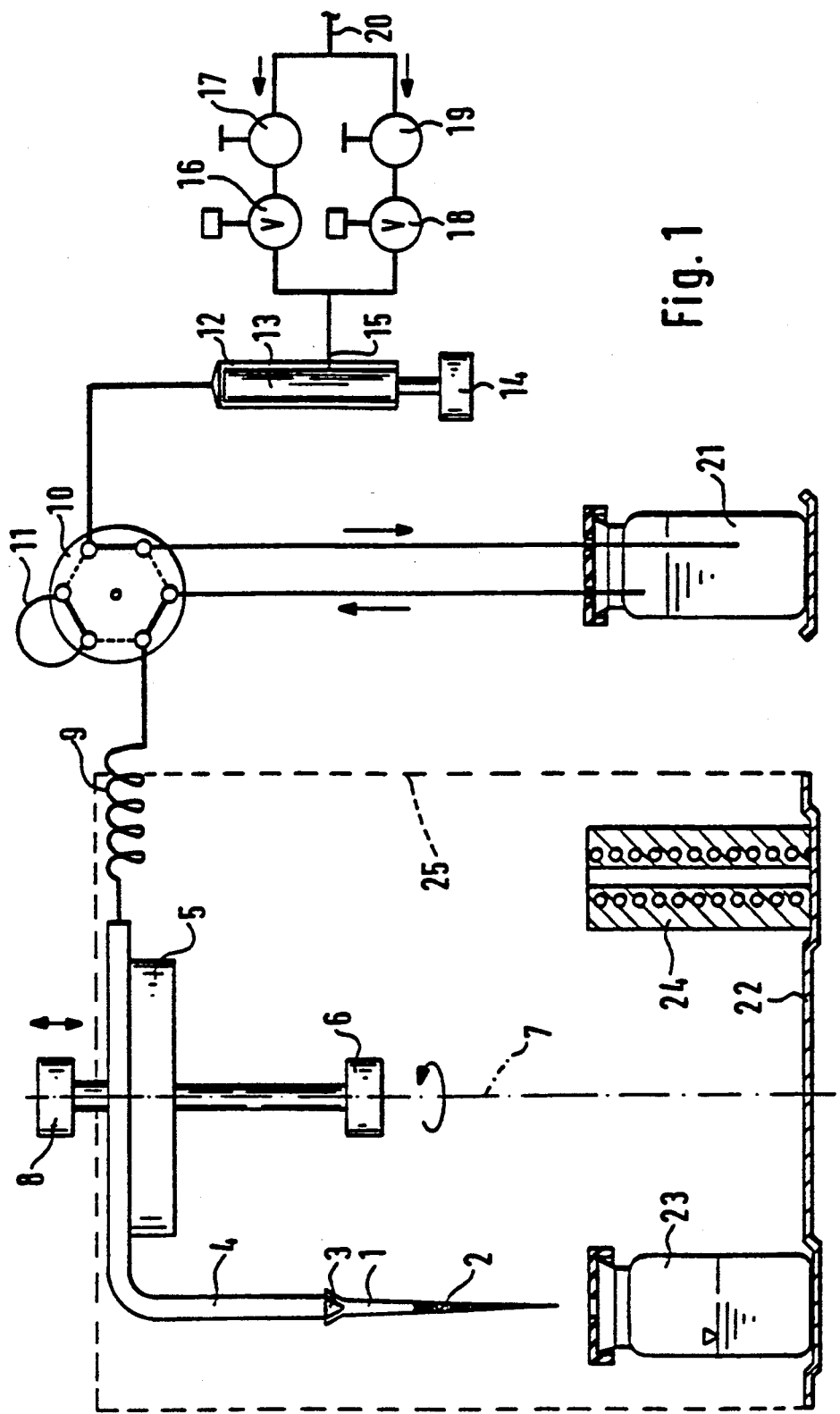
FIG. 1 is a schematic diagram of an apparatus of the invention.

FIG. 1 shows an apparatus according to the invention which may be used for sequencing proteins or peptides. The apparatus comprises a reactor 1 which is preferably a pipette tip. The interior of the reactor 1 is filled with a matrix 2 for holding in place the proteins which are to be sequenced. The matrix 2 may comprise glass fibers, membranes, or porous or non-porous particles which bear the protein or peptide on their surfaces.

The upper end of the pipette tip 1 fits into a receptor 3 which is connected to a capillary 4. The lower end of the pipette tip 1 has an opening through which liquid can enter or leave the reactor 1. The capillary 4 is fixed to a rotor arm 5 which can be rotated by means of a motor 6 around an axis 7 and which can be lowered or raised along the direction of the axis 7 by means of a motor 8. The end of capillary 4 which is distant from the reactor 1 is connected to a metering pump 12 via a capillary loop 9 and a six-way switching valve 10. In the embodiment shown, the metering pump is designed as a syringe comprising a piston 13 which can be moved back and forth by a motor 14. The switching valve 10 comprises a capillary 11 which connects two ports of the valve such that there is a direct connection between the metering pump 12 and the pipette tip 1 when the valve is in the position indicated by dotted lines.

Connected to the metering pump 12 is a gas supply line 15 through which nitrogen or argon can be supplied. The gas can be supplied at two different flow rates which are adjustable by devices 17 and 19, respectively, through valves 16 or 18. One gas stream serves to purge the system and to dry the reactor, while the other is used as a bubble stream to transfer gaseous trimethylamine (TMA) from the bottle 21 into the reactor 1. To purge the system, the valve 10 should be switched into the position indicated by dotted lines. The two gas streams are introduced via a common input line 20.

Arranged on a circular tray 22 are a plurality of containers such as bottle 23 and devices such as oven 24. The containers and devices (i.e. process stations) are arranged in a circular fashion so that they can be accessed by the reactor 1 by turning the rotor arm 5 by a certain angle around the axis 7. Also provided on the tray 22 is a park device (not shown) which allows attachment and detachment of the reactor 1 to or from the receptor 3, respectively. The park device comprises an opening for holding the reactor 1 in place while the receptor 3 is free to move to, for example, one of the bottles on the tray to take in or to eject liquid. The reactor 1 can also be positioned in an oven 24 to initiate or accelerate the desired chemical reactions. A second oven having a different temperature than the first one can additionally be provided on the tray 22.

The liquids used during the process can be precisely metered by appropriate control of the piston 13 of the syringe 12 when it is connected via the switching valve 10 and the loop 9 to the capillary 4. Delivery of fluids out of the capillary 4 or the reactor 1 into a bottle is performed either by a positive displacement motion of the piston 13 or by purging with a stream of inert gas through gas supply line 15. As shown in FIG. 1, there is a ring gap between the piston 13 and the wall of the syringe 12 so that gas from the supply line 15 can flow past the piston 13 to the valve 10.

A glass cylinder 25 which is sealed at its upper and lower ends forms the boundary of an area which can be purged with inert gas. All elements and substances within this area can thus be protected from the access of oxygen.

For protein sequencing, it is preferred that the bottles 23 on the tray 22 contain ethyl acetate, butyl chloride, heptane, PITC, trifluoroacetic acid (TFA), and TFA/water, respectively. Another bottle serves as a waste container, while yet another holds the ATZ amino acid while the butyl chloride (used for extraction) is removed and the ATZ amino acid is reconstituted in TFA/water.

Figure 2A:
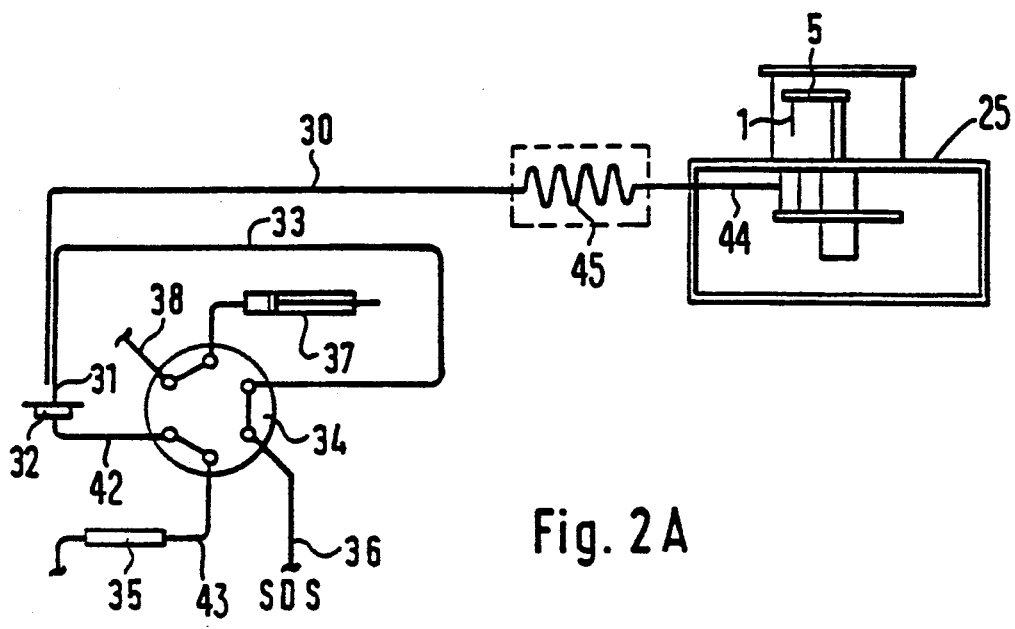
FIGS. 2A and 2B are schematic diagrams illustrating two process steps used in a method of protein sequencing wherein an apparatus according to the invention is coupled to a liquid chromatograph.
Figure 2B:
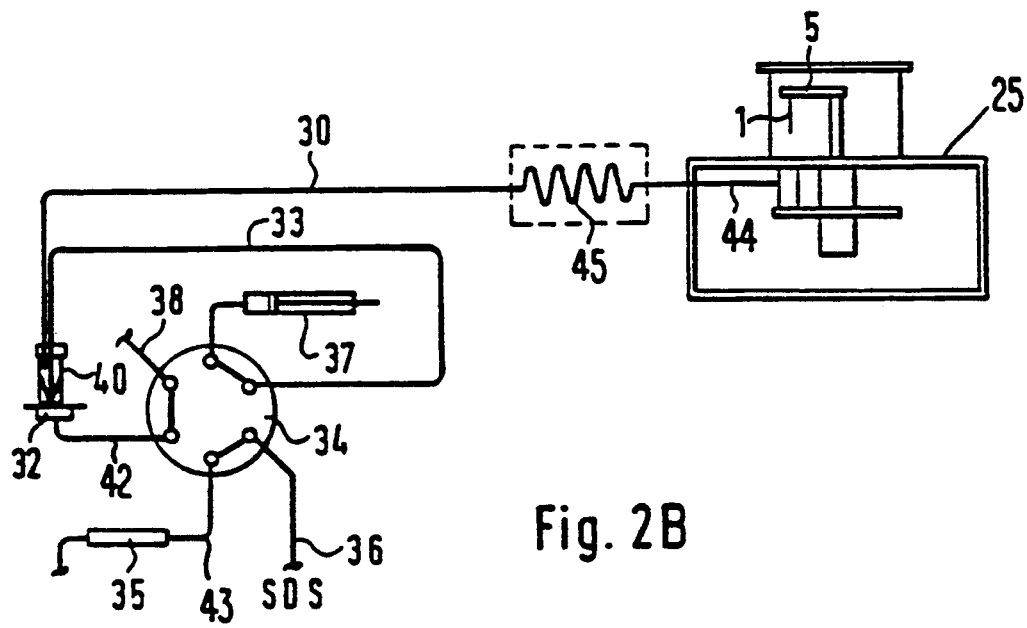

FIGS. 2A and 2B depict the coupling of an apparatus according to the present invention to a liquid chromatograph. Such an arrangement can be used in protein sequencing for the chromatographic determination of the PTH amino acids. FIGS. 2A and 2B illustrate two of the process steps in the sequencing of proteins performed in accordance with the above mentioned Edman degradation process. FIG. 2A illustrates the step wherein the PTH amino acid which is provided from the liquid processing apparatus of the invention is chromatographically analyzed.

In FIG. 2A, reference numeral 25 indicates the housing of the liquid processing apparatus of the invention shown in more detail in FIG. 1. The rotor arm 5 and the reactor 1 are also shown. A capillary 44 is connected to a capillary loop 45, which can be heated. The ATZ amino acid (dissolved in TFA/water) is first transferred into the heated capillary loop 45, which can accommodate 100 microliters of liquid. The liquid plug containing the ATZ amino acid and having a volume smaller than 100 microliters is positioned in the middle of this capillary and held there in place for about 10 minutes. During this time, the ATZ amino acid is converted to the PTH amino acid, which is then chromatographically analyzed.

Figure 3:
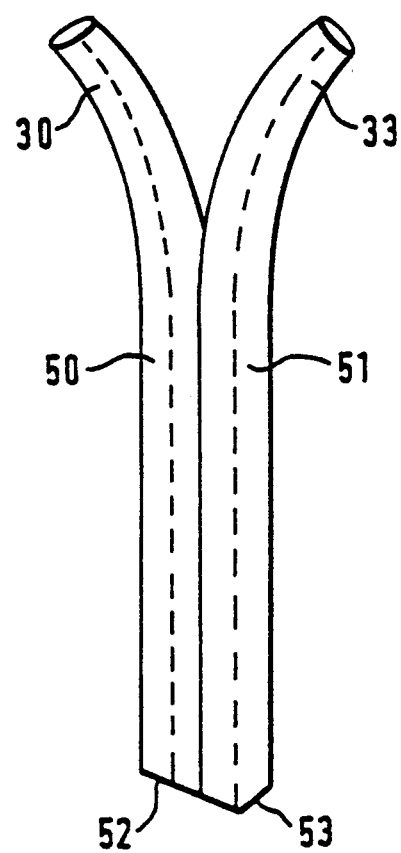
FIG. 3 is a more detailed view of the double-needle shown in FIGS. 2A and 2B.

The output end of the loop 45 is connected via a capillary 30 to a double-needle 31 which comprises two tips at its end, one of which is connected to the capillary 30. The double-needle is shown in more detail in FIG. 3. As can be seen from FIG. 3, the double-needle comprises a first hollow needle 50 and a second hollow needle 51 connected to the capillaries 30 and 33, respectively. The two needles are fixed to each other by, for example, welding or soldering, and can be raised or lowered together. The second hollow needle 51 extends beyond the first needle 50, as shown in FIG. 3.

Referring again to FIGS. 2A and 3, the second end 53 of the double-needle 31 is inserted into an injection port 32 of a liquid chromatograph. The double-needle is designed such that the opening 53 does not interfere with the opening 52 when opening 53 is inserted into the injection port 32. Thus, no liquid can reach the injection port through the end 52. The injection port 32 typically comprises a seat into which the tip 53 of the double-needle tightly fits. Injection port 32 is connected via capillary 42 to a port of a six-port switching valve 34, which is connected via capillary 43 to a separation column 35 of a liquid chromatograph. Capillary 33 is connected to another port of valve 34. Capillary 36 is connected with its first end to a further port of the valve 34 and with its second end to a solvent delivery system (SDS), which typically comprises a high-pressure pump. With the position of valve 34 shown in FIG. 2A, there is a hydraulic connection between the solvent delivery system (SDS), capillary 33, and separation column 35. Thus, a PTH amino acid which has previously been sucked into capillary 33 is pushed to separation column 35 by a stream of solvent provided by the solvent delivery system. Also connected to the valve 34 is a syringe 37, the output of which can be coupled either to a conduit 38 for ejection of waste fluid or, after switching the valve 34 to its second position, to the capillary 33.

In the next step (not shown), the double-needle 31 is lifted off the injection port 32 and positioned in a waste vial. The capillaries then are purged and dried in preparation for the next step. In the following step, also known as the conversion step, the next ATZ amino acid of the protein to be sequenced is positioned in the capillary loop 45, converted to PTH amino acid by application of heat as described above, and then transferred through end 52 of double needle 31 into vial 40.

FIG. 2B illustrates the step wherein the PTH amino acid has been transferred to the vial 40 and the switching valve 34 has been switched to the position wherein the syringe 37 is connected to the capillary 33. The interior walls of the vial 40 are tapered so that the PTH amino acid is collected at the peak of the cone. The double-needle 31 is positioned in the vial 40 such that tip 53 connected to the capillary 33 almost touches the bottom of the vial 40 so that very small amounts of liquid can be sucked in.

The syringe 37 next is actuated to draw a suitable aliquot of the PTH amino acid into the capillary 33, while the remainder is stored in the vial for any further analysis which may be required. Then, the vial 40 is removed, the lower tip 53 of the double-needle is placed on the injection port 32, and the valve 34 is switched to its second position so that the PTH amino acid can be transferred by the solvent stream from the SDS to the column 35 for chromatographic separation. Thereafter, a new cycle for determining the next amino acid in the protein starts.

Thus, a complete cycle preferably comprises the following steps:
(1) chromatographic analysis of the $(n-1)^{th}$ PTH amino acid by injection into column 35;
(2) purging and drying the capillaries;
(3) converting the $n^{th}$ ATZ amino acid into PTH amino acid by heating in capillary loop 45;
(4) transferring PTH amino acid into vial 40;
(5) sucking PTH amino acid into capillary 33; and
(6) chromatographic analysis of the $n^{th}$ PTH amino acid by injection into column 35.

The injection port 32, the valve 34, and the syringe 37 may be parts of the injection system of a liquid chromatograph such as, for example, the Hewlett-Packard model HP 1090 Liquid Chromatograph. The sequencer described in connection with FIGS. 2A and 2B preferably is controlled by a computer so that the Edman process can carried out sequentially without an operator.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. An apparatus for stepwise performance of chemical reactions, comprising:
    a tube system having a first end and a second end through which at least one fluid can enter or leave the tube system;
    a hollow, open-ended reactor compartment having a first end and a second end through which at least one fluid can enter or leave the reactor compartment, wherein said first end of said reactor compartment is detachably coupled to the first end of the tube system;
    means coupled to said tube system for metering in a first direction a first solution containing a first chemical compound from a source of said first solution into the second end of said reactor compartment when said first end of said reactor compartment is attached to the first end of the tube system;
    means for detaching said reactor compartment containing said first chemical compound from said first end of said tube system;
    means coupled to said tube system for metering in said first direction a second solution containing a second chemical compound from a source of said second solution into said first end of said tube system;
    means for reattaching said reactor compartment containing said first chemical compound to said first end of said tube system; and
    means coupled to said tube system for metering in a second direction opposite from said first direction said second solution contained in said tube system into said reactor compartment through said first end of said reactor compartment which is attached to the first end of the tube system to cause said second chemical compound to come into contact and react with said first chemical compound in said reactor compartment.

2. The apparatus of claim 1 further comprising a plurality of process stations positioned proximate the first end of the tube system.

3. The apparatus of claim 2 wherein the process stations are selected from the group consisting of bottles of reagents or solvents, waste containers, and ovens.

4. The apparatus of claim 2 further comprising positioning means for selectably positioning the first end of the tube system at any of the process stations.

5. The apparatus of claim 4 wherein the positioning means comprises:
    a rotor arm connected to the first end of the tube system;
    rotating means connected with the rotor arm for rotating the rotor arm around an axis for selectably accessing a process station arranged on a circle around the axis; and
    displacing means connected with the rotor arm for raising or lowering the rotor arm.

6. The apparatus of claim 5 wherein at least one of said processing stations is a device positioned proximate the first end of the tube system, said device being designed for receiving the reactor compartment.

7. The apparatus of claim 4 wherein the positioning means comprises an X, Y-drive connected to the first end of the tube system.

8. The apparatus of claim 1 wherein the reactor compartment is filled with a matrix which holds in place said first and second chemical compounds.

9. The apparatus of claim 1 wherein the reactor compartment comprises a pipette tip.

10. The apparatus of claim 1 further comprising means connected to the tube system for supplying a stream of inert gas to the tube system.

11. The apparatus of claim 1 further comprising a double-needle which comprises two hollow needles of different lengths connected parallel to each other, one of the hollow needles being connected to the tube system and the other hollow needle being selectably connectable via a switching valve to a syringe or to a solvent delivery system.

12. The apparatus of claim 1 wherein the stepwise performance of chemical reactions comprises determining the sequence of amino acids in a peptide.

13. A method for stepwise performance of chemical reactions, comprising the steps of:
   metering in a first direction a first solution containing a first chemical compound from a source of said first solution into a second end of a hollow, open-ended reactor compartment that is detachably coupled at a first end with a first end of a tube system;
   detaching said reactor compartment containing said first chemical compound from said first end of said tube system;
   metering in said first direction a second solution containing a second chemical compound from a source of said second solution into said first end of said tube system;
   reattaching said reactor compartment containing said first chemical compound to said first end of said tube system; and
   metering in a second direction opposite from said first direction said second solution contained in said tube system into said reactor compartment through said first end of said reactor compartment which is attached to the first end of the tube system, thereby causing said second chemical compound to come into contact and react with said first chemical compound in said reactor compartment.

14. The method of claim 13 wherein the first end of the tube system is positioned by rotating the first end around an axis.

15. The method of claim 13 wherein the first end of the tube system is positioned by raising or lowering the first end of the tube system.

16. The method of claim 13 wherein the reactor compartment comprises a pipette tip.

17. The method of claim 13 wherein the reactor compartment is filled with a matrix which holds in place said first and second chemical compounds.

18. The method of claim 13 wherein the first and second solutions are passed into or out of the tube system using a metering device which is coupled to the tube system.

19. The method of claim 13 wherein the stepwise performance of chemical reactions comprises determining the sequence of amino acids in a peptide.

* * * * *